United States Patent
Contino et al.

(10) Patent No.: US 12,121,759 B2
(45) Date of Patent: Oct. 22, 2024

(54) METHOD OF SUPPLYING OXYGEN TO AN AIRCRAFT OXYGEN MASK

(71) Applicant: AVOX Systems Inc., Lancaster, NY (US)

(72) Inventors: Joseph Contino, East Amherst, NY (US); Steven Sanfilippo, Lancaster, NY (US)

(73) Assignee: AVOX SYSTEMS INC., Lancaster, NY (US)

( * ) Notice: Subject to any disclaimer, the term of this patent is extended or adjusted under 35 U.S.C. 154(b) by 378 days.

(21) Appl. No.: 16/918,597

(22) Filed: Jul. 1, 2020

(65) Prior Publication Data

US 2022/0001217 A1  Jan. 6, 2022

(51) Int. Cl.
| | |
|---|---|
| A62B 7/14 | (2006.01) |
| A61B 5/145 | (2006.01) |
| A62B 7/02 | (2006.01) |
| A62B 9/00 | (2006.01) |
| B64D 11/00 | (2006.01) |

(52) U.S. Cl.
CPC .......... *A62B 7/14* (2013.01); *A62B 7/02* (2013.01); *A62B 9/006* (2013.01); *B64D 11/00* (2013.01); *A61B 5/14542* (2013.01); *B64D 2231/025* (2013.01)

(58) Field of Classification Search
CPC .... A62B 7/14; A62B 7/02; A62B 7/00; A62B 7/04; A62B 9/006; B64D 11/0632; B64D 2231/025; B64D 2231/02; B64D 2231/00; A61B 5/14542; A61B 5/145
See application file for complete search history.

(56) References Cited

U.S. PATENT DOCUMENTS

| | | | | |
|---|---|---|---|---|
| 2006/0118115 | A1* | 6/2006 | Cannon | A62B 7/04 |
| | | | | 128/204.26 |
| 2009/0188504 | A1* | 7/2009 | Siska, Jr. | A62B 9/02 |
| | | | | 128/205.21 |

(Continued)

FOREIGN PATENT DOCUMENTS

CN    107866012    4/2018

OTHER PUBLICATIONS

Rojas-Camayo et al., "Reference values for oxygen saturation from sea level to the highest human habitation in the Andes in acclimatised persons", Oct. 2017, Throax, vol. 73, No. 8, 776-777 (Year: 2017).*

(Continued)

*Primary Examiner* — Joseph D. Boecker
*Assistant Examiner* — Brian T Khong
(74) *Attorney, Agent, or Firm* — Kilpatrick Townsend & Stockton LLP

(57) ABSTRACT

A method of supplying oxygen to an oxygen mask for an aircraft includes detecting, with at least one sensor and during a first time period, a first blood-oxygen saturation level at a first altitude. The method may also include detecting, with the at least one sensor and during a second time period, a second blood-oxygen saturation level at a second altitude that is different from the first altitude. The method may include determining a minimum flow rate of a gas that includes oxygen for the second altitude such that the second blood-oxygen saturation level at least matches the first blood-oxygen saturation level at the same altitude.

7 Claims, 2 Drawing Sheets

(56) References Cited

U.S. PATENT DOCUMENTS

| | | | | |
|---|---|---|---|---|
| 2011/0000490 A1* | 1/2011 | Gillotin | .................... | A62B 7/14 |
| | | | | 128/204.26 |
| 2012/0160244 A1* | 6/2012 | Sharma Hk | ........... | A61M 16/12 |
| | | | | 128/204.23 |
| 2015/0174359 A1* | 6/2015 | Elliott | ................ | A61M 16/024 |
| | | | | 128/204.22 |
| 2016/0303405 A1* | 10/2016 | Elliott | ................ | A61B 5/0816 |

OTHER PUBLICATIONS

Hinkelbein et al., "Oxygen Delivery Comparison of Two Constant-Flow Masks During Flight to 6863 m", May 2006, Aviation, Space, and Environmental Medicine, vol. 77, No. 5, pp. 540-544 (Year: 2006).*

Cabler, "Technical Standard Order, Passenger Oxygen Mask Assembly, Continuous Flow", May 21, 2008, Department of Transportation, Federal Aviation Administration, All Pages (Year: 2008).*

Chapter 6—Aircraft Systems, Pilot's Handbook of Aeronautical Knowledge, 2008, 42 pages.

International Application No. PCT/US2021/039391, International Search Report and Written Opinion mailed on Oct. 21, 2021, 12 pages.

International Application No. PCT/US2021/039391, International Preliminary Report on Patentability mailed on Jan. 12, 2023, 8 pages.

* cited by examiner

METHOD OF SUPPLYING OXYGEN TO AN AIRCRAFT OXYGEN MASK

FIELD OF THE INVENTION

The field of the invention relates to oxygen masks, such as oxygen masks for an aircraft, and, more particularly, to methods of supplying supplemental oxygen to an oxygen mask.

BACKGROUND

As a passenger of an aircraft or other passenger vehicle travels at altitude, the partial pressure of oxygen in the environment decreases, and without the pressurization of aircraft cabins, the passengers of such an aircraft would encounter environmental hypoxia. In the event that an aircraft cabin encounters depressurization of the cabin while in flight at altitude, various regulations require that aircraft manufacturers install equipment that will allow pilots and passengers to obtain supplemental oxygen until the aircraft can descend to lower altitudes (typically 10,000 ft.). The current minimum requirements for the design, construction, and performance of continuous flow oxygen masks are provided in the standard SAE (Society of Automotive Engineers) AS8025. Per the standard, each oxygen mask includes a face piece with valves as required, a mask suspension device, a reservoir or re-breather bag, a length of tubing of connection to the oxygen supply source, and a means for allowing the crew to determine if oxygen is being delivered to the mask.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, a method of supplying oxygen to an oxygen mask for an aircraft includes detecting, with at least one sensor and during a first time period, a first blood-oxygen saturation level at a first altitude. The method includes detecting, with the at least one sensor and during a second time period, a second blood-oxygen saturation level at a second altitude that is greater than the first altitude. The method may also include determining a minimum flow rate of a gas comprising oxygen for the second altitude such that the second blood-oxygen saturation level at least matches the first blood-oxygen saturation level at the same altitude.

In some embodiments, the method includes controlling, by a controller, a flow of the gas comprising oxygen to the oxygen mask such that the gas is supplied at the minimum flow rate. In various embodiments, controlling the flow of the gas comprising oxygen includes determining a flow duration of the gas having a first concentration of oxygen such that the second-blood oxygen saturation level at least matches the first blood-oxygen saturation level at the same altitude. The method may include controlling the flow of the gas such that the gas having the first concentration of oxygen is supplied to the oxygen mask for the flow duration. In various cases, the first concentration of oxygen is 100% oxygen.

In various embodiments, the flow duration is a first flow duration, and controlling the flow of the gas comprising oxygen includes determining a second flow duration of the gas having a second concentration of oxygen, where the second concentration of oxygen is less than the first concentration of oxygen. The method may include controlling the flow of the gas such that the gas having the second concentration of oxygen is supplied after the first flow duration and for the second flow duration. In certain embodiments, the first flow duration is less than the second flow duration.

In some aspects, controlling the flow of the gas includes supplying the gas at a flow rate from 0.2 L/min to 1.7 L/min. In certain cases, the second altitude is at least 12,000 feet. In some embodiments, the method includes generating an alert based on the second blood-oxygen saturation level being less than the first blood-oxygen saturation level. In certain embodiments, the first time period and the second time period are each from 30 seconds to 180 seconds. In various embodiments, at least one of the first time period or the second time period is 120 seconds.

In various cases, the method includes detecting, with the at least one sensor and during a third time period, a third blood-oxygen saturation level at a third altitude, where the third altitude is greater than the first altitude and greater than the second altitude, and determining a minimum flow rate of the gas comprising oxygen for the third altitude.

According to certain embodiments of the present invention, a method of supplying oxygen to an oxygen mask includes simulating, with a testing system, an atmosphere at a first altitude, and detecting, with a sensor, a blood-oxygen saturation level at the first altitude. The method also includes determining a minimum flow rate for the first altitude of a gas comprising oxygen such that the detected blood-oxygen saturation level at least matches a predetermined blood-oxygen saturation level.

In various embodiments, the method includes controlling a flow of the gas to the oxygen mask such that the gas flows at the minimum flow rate and such that the detected blood-oxygen saturation level at least matches the predetermined blood-oxygen saturation level. In some examples, controlling the flow of the gas includes determining a first flow of the gas having a first oxygen concentration and a first flow duration and determining a second flow of the gas having a second oxygen concentration and a second flow duration, where the second oxygen concentration is less than the first oxygen concentration. The method may include supplying the first flow of the gas comprising the first oxygen concentration for the first flow duration and supplying the second flow of the gas comprising the second oxygen concentration for the second flow duration after the first flow duration. In some embodiments, the first oxygen concentration is 100% oxygen, and the first flow duration is less than the second flow duration.

In some cases, the detected blood-oxygen saturation level is a first detected blood-oxygen saturation level, and the method includes simulating, with the testing system, an atmosphere at a second altitude, where the second altitude is greater than the first altitude, and detecting, with the sensor, a second blood-oxygen saturation level at the second altitude. The method may include determining a minimum flow rate of the gas having for the second altitude such that the detected blood-oxygen saturation level at the second altitude at least matches the predetermined blood-oxygen saturation level.

In various aspects, the predetermined blood-oxygen saturation level is at a predetermined altitude, and the predetermined altitude is less than the first altitude. In some examples, determining the minimum flow rate of the gas includes determining a flow rate of 0.2 L/min to 1.7 L/min when the first altitude is less than or equal to 35,000 feet. In various embodiments, the method includes generating an alert based on the detected blood-oxygen saturation level being less than the predetermined blood-oxygen saturation level. In some cases, determining the minimum flow rate of the gas to the oxygen mask includes determining the minimum flow rate of the gas such that the detected blood-oxygen saturation level is at least 90%.

Various implementations described herein can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Described herein are methods for supplying oxygen to an oxygen for an aircraft and associated systems. In various examples, the method includes detecting with at least one sensor an actual blood-oxygen saturation level at a first altitude. In some cases, the first altitude is simulated. The method may include determining a minimum flow rate for the first altitude of a gas containing oxygen such that the detected blood-oxygen saturation level at least matches a predetermined blood-oxygen saturation level. In some cases, the predetermined blood-oxygen saturation level is detected by the at least one sensor at a base altitude that is different from the first altitude. The method may include supplying the gas containing oxygen at the minimum flow rate for the first altitude via an oxygen mask.

Figure 1:
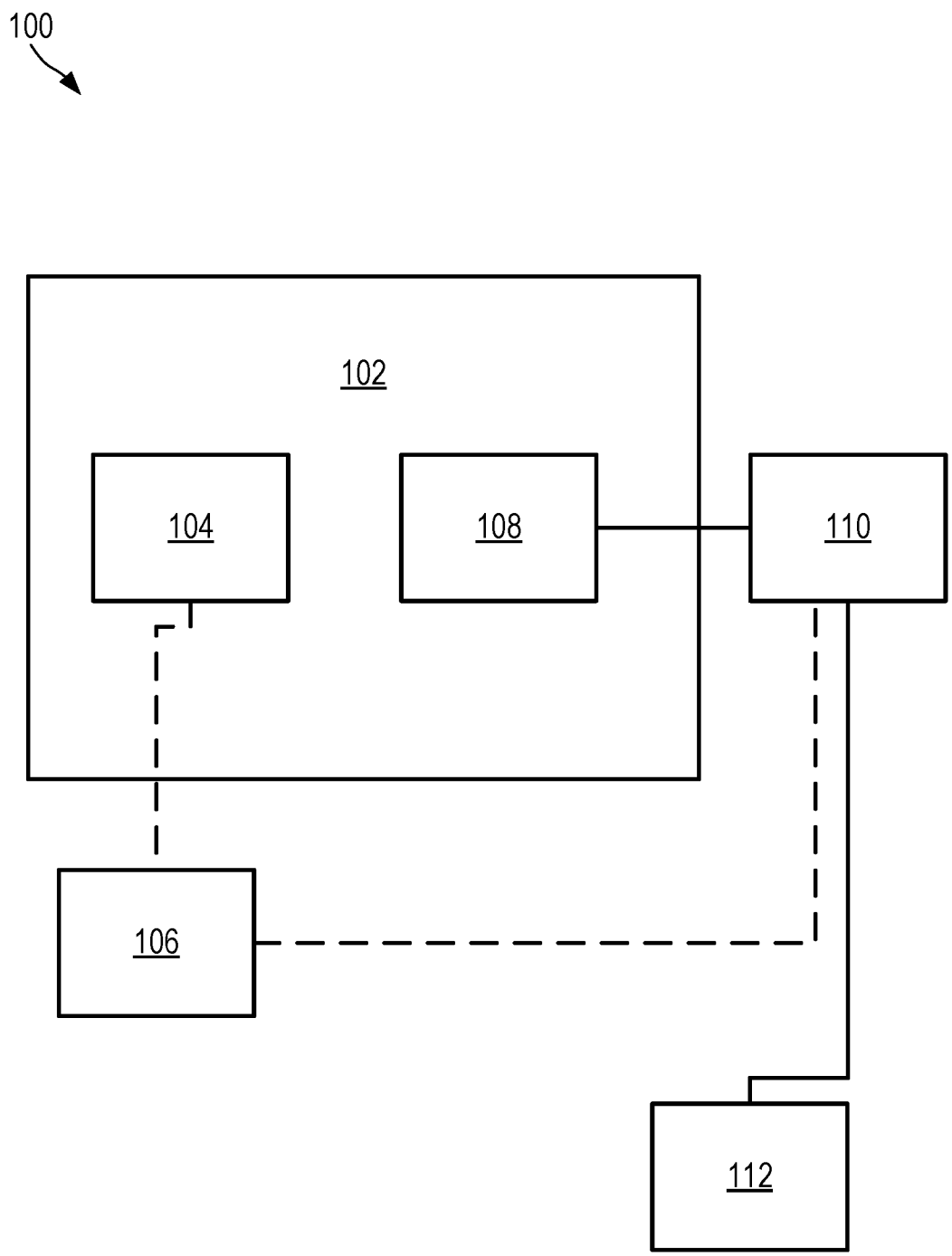
FIG. 1 illustrates a testing system according to certain embodiments of the present invention.

FIG. 1 illustrates an example of a testing system 100 for supplying a gas containing oxygen according to various embodiments. In various embodiments, the testing system 100 includes a testing chamber 102, one or more blood-oxygen saturation sensors 104, and an optional controller 106. The testing system 100 may also include a gas supply 112 and a flow controller 110. An oxygen mask 108 for an aircraft may be within the testing chamber 102 and in fluid communication with the flow controller 110 and the gas supply 112 such that the gas containing oxygen can be selectively supplied to the oxygen mask 108.

The testing chamber 102 may include various devices and/or components for simulating an atmosphere at an altitude within the testing chamber 102. In certain aspects, the testing chamber 102 may be controlled to simulate various altitudes, such as altitudes that an aircraft may operate at during a flight. As some non-limiting examples, the testing chamber 102 may be controlled to simulate an altitude of about 15,000 ft., about 18,000 ft., about 20,000 ft., about 25,000 ft., about 30,000 ft., about 35,000 ft., and/or about 40,000 ft. In other examples, the testing chamber 102 may be controlled to simulate an altitude less than about 10,000 ft., greater than about 40,000 ft., and/or at various other altitudes between 10,000 ft. and 40,000 ft. In various aspects, the testing chamber 102 may be controlled by the controller 106, although it need not be in other examples.

The blood-oxygen saturation sensor 104 may be various suitable devices or combinations of devices for measuring a blood-oxygen saturation level of a user. As one non-limiting example, the blood-oxygen saturation sensor 104 may be an oximeter. While a single blood-oxygen saturation sensor 104 is illustrated, in other examples, additional blood-oxygen sensors 104 may be utilized, such as two blood-oxygen saturation sensors 104. In various cases, the blood-oxygen saturation sensor 104 may measure the blood-oxygen saturation level of a user within the testing chamber 102 such that the blood-oxygen saturation sensor 104 measures the blood-oxygen saturation level of the user while the user is at various simulated altitudes. In one non-limiting example, the blood-oxygen saturation sensor 104 is positionable on a portion of the user, including but, not limited to, the user's forehead.

The controller 106 is communicatively coupled with the blood-oxygen saturation sensor 104 and the flow controller 110, and may have various suitable processing and/or memory components for controlling the flow controller 110 as discussed in detail below. In some cases, the controller 106 may be outside of the testing chamber 102 (as illustrated in FIG. 1), although in other examples, the controller 106 may be within the testing chamber 102.

The flow controller 110 may be various suitable devices and/or mechanisms that may be selectively controlled to control a supply of the gas containing oxygen from the gas supply 112 to the oxygen mask 108. The flow controller 110 may be within the testing chamber 102 or outside of the testing chamber 102 as desired. The gas supply 112 may include one or more sources of the gas containing oxygen.

In various examples, the testing system 100 may be utilized to perform a testing process for one or more oxygen masks 108. In some cases, the testing process may include determining a baseline blood-oxygen saturation level simulating an atmosphere at a baseline altitude with the testing chamber 102 for a baseline predetermined time period, and detecting the blood-oxygen saturation level with the sensor 104 as a baseline blood-oxygen saturation level. In certain embodiments, the baseline predetermined time period may be at least a minimum time period needed to adjust the testing chamber 102 to simulate the baseline altitude. In various embodiments, the minimum time period may optionally be at least 30 seconds. In some examples, the baseline predetermined time period may be from about 30 seconds to about 180 seconds. In one non-limiting examples, the baseline predetermined time period may be 120 seconds. In other examples, the baseline predetermined time period may be less than 30 seconds and/or greater than 180 seconds. In some cases, the baseline blood-oxygen saturation level at the baseline altitude may be the user's blood oxygen-saturation level at an altitude at which the user breathes without the use of supplemental oxygen as specified by various regulations or standards, and may be the blood-oxygen saturation level that the oxygen mask tries to return a user to during an emergency situation at elevated altitudes. As some non-limiting examples, the baseline altitude may be 10,000 ft. and/or 14,000 ft. In some cases, the baseline blood-oxygen saturation level and/or the baseline altitude may be determined prior to testing with the oxygen mask 108, and the oxygen mask 108 may optionally be omitted during such a process of determining the baseline blood-oxygen saturation level. In other examples, the oxygen mask 108 may be provided with the user in the testing chamber 102 for determining the baseline blood-oxygen saturation level.

The testing process may include simulating an atmosphere at a first elevated altitude with the testing chamber 102 that is greater than the baseline (or predetermined) altitude. The first elevated altitude may be simulated for a predetermined time period. In some cases, the first elevated altitude may be various altitudes greater than the baseline altitude, such as about 15,000 ft., about 18,000 ft., about 20,000 ft., about 25,000 ft., about 30,000 ft., about 35,000 ft., about 40,000 ft., and/or various other altitudes as desired. In certain embodiments, the predetermined time period may be at least a minimum time period needed to adjust the testing chamber 102 to simulate the first elevated altitude. In various embodiments, the minimum time period may optionally be at least 30 seconds. In some examples, the predetermined time period may be from about 30 seconds to about 180 seconds. In one non-limiting examples, the predetermined time period may be 120 seconds. In other examples, the predetermined time period may be less than 30 seconds and/or greater than 180 seconds.

In various cases, the method may include detecting a blood-oxygen saturation level of the user within the testing chamber 102 with the sensor 104 while the first elevated altitude is being simulated. The detected blood-oxygen saturation level may be transmitted to the controller 106 as data via various suitable communication mechanisms as desired (e.g., wirelessly, wired, etc.) or the detected blood-oxygen saturation level may otherwise be recorded.

The controller 106 may determine a minimum flow rate of a gas containing oxygen for the first elevated altitude such that the detected blood-oxygen saturation level at least matches the baseline (or predetermined) blood-oxygen saturation level. In certain aspects, determining the minimum flow rate may optionally include determining a flow rate of about 0.2 L/min. to about 1.7 L/min. when the first elevated altitude is less than or equal to 35,000 ft., although it need not in other examples. In some cases, determining the minimum flow rate may include determining a minimum flow rate of the gas such that the detected blood-oxygen saturation level is at least 90% of the baseline blood-oxygen level, and as used herein, "matches" refers to at least 90%. Moreover, in certain cases, the minimum flow rate may allow for the detected blood-oxygen saturation levels to be greater than the baseline blood-oxygen saturation levels. In certain cases, determining the minimum flow rate may include determining a first flow of the gas comprising a first oxygen concentration and a first flow duration and determining a second flow of the gas comprising a second oxygen concentration and a second flow duration, where the second oxygen concentration is less than the first oxygen concentration. In some examples, the first oxygen concentration is optionally 100% oxygen. In various examples, the second flow duration may optionally be greater than the first flow duration.

Optionally, the controller 106 may generate an alert based on the detected blood-oxygen saturation level being less than the baseline blood-oxygen saturation level. In such examples, various suitable alerts may be generated, including, but not limited to, a visual alert on a visual indicator or other suitable device, an audio alert on a speaker or other suitable device, and/or a text alert on a screen or other device having a user interface as desired.

In some examples, the testing process may include controlling, by the controller 106 or otherwise, the flow controller 110 such that the gas containing oxygen is supplied to the oxygen mask 108 at the determined minimum flow rate. In examples where the first flow and the second flow are determined by the controller 106, the process may include controlling, by the controller 106, the flow controller 110 such that the oxygen mask 108 is provided with the first flow of the gas containing the first oxygen concentration for the first flow duration and such that the oxygen mask 108 is provided with the second flow of the gas containing the second oxygen concentration for the second flow duration after the first flow duration. The testing process may be repeated at various other elevated altitudes relative to the baseline altitude as desired.

Figure 2:
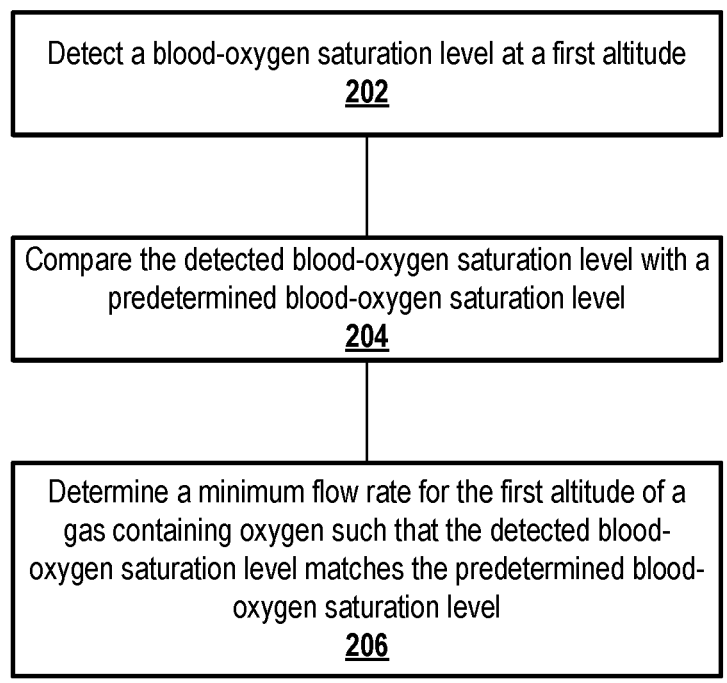
FIG. 2 illustrates a method of supplying oxygen to an oxygen mask according to certain embodiments of the present invention.

FIG. 2 illustrates a method of controlling a supply of a gas containing oxygen according to various embodiments.

In a block 202, the method includes detecting a blood-oxygen saturation level at a first altitude. In some examples, the blood-oxygen saturation level of a user is detected with a sensor such as the sensor 104. In various examples, the first altitude may be simulated, such as via the testing chamber 102, although it need not be simulated in other examples. In certain aspects, the first altitude may be greater than a baseline altitude. In some non-limiting examples, the first altitude may be greater than 10,000 ft., and in some cases, may be at least 12,000 ft. In some cases, the blood-oxygen saturation level is detected for the predetermined time period while the user is at the first altitude.

In a block 204, the method includes comparing the detected blood-oxygen saturation level of the user at the first altitude with a baseline blood-oxygen saturation level of the user at the baseline altitude. In some cases, the baseline blood-oxygen saturation level may be predetermined.

In a block 206, the method includes determining a minimum flow rate for the first altitude of the gas containing oxygen such that the detected blood-oxygen saturation level at the first altitude at least matches the baseline blood-oxygen saturation level at the baseline altitude. In various aspects, determining the minimum flow rate optionally includes determining a flow rate of from about 0.2 L/min. to about 1.7 L/min. when the first altitude is less than or equal to 35,000 feet. In one non-limiting example, the method may include a flow rate of about 0.3 L/min. at an altitude of 15,000 ft., a flow rate of about 0.4 L/min. at an altitude of 20,000 ft., a flow rate of 0.7 L/min. at an altitude of 25,000 ft., a flow rate of about 1.0 L/min. at an altitude of 30,000 ft., and a flow rate of 1.7 L/min. at an altitude of 35,000 ft.

Optionally, block 206 may include determining a first flow of the gas comprising a first oxygen concentration and a first flow duration and determining a second flow of the gas comprising a second oxygen concentration and a second flow duration such that the detected blood-oxygen saturation level at least matches the baseline blood-oxygen saturation level at the same altitude. In such examples, the first oxygen concentration is greater than the second oxygen concentration, and in one non-limiting example, the first oxygen concentration is 100% oxygen. Optionally, block 206 may include generating an alarm based on the detected blood-oxygen saturation level being less than (or not matching) the baseline blood-oxygen saturation level. Block 206 may optionally include controlling a flow controller for the gas containing oxygen such that the gas containing oxygen is supplied to the oxygen mask at the minimum flow rate.

In certain aspects, blocks 202, 204, and 206 may be repeated as desired for other users and/or for other altitudes. For example, the process may be performed at a plurality of altitudes for a particular user, and the blocks 202, 204, and 206 may be repeated for each altitude of the plurality of altitudes.

The embodiments described herein may provide improved control of an oxygen supply to an oxygen mask compared to traditional methods that utilize a breathing machine. In particular, the current minimum requirements for the design, construction, and performance of oxygen masks utilize a breathing machine to determine a required oxygen flow to the mask. More specifically, the breathing machine has a chamber in which a mask is placed, and a flow rate of oxygen to the mask is established based on a measured gas concentration within the chamber. These existing systems do not accurately model the way that an oxygen mask works and/or how the pulmonary system of the user of the mask works, and therefore determine oxygen flow rates that are higher than are actually required to keep the passenger at safe levels. Such higher levels lead to an oversupply of oxygen to the mask, thereby depleting the oxygen supply more quickly than needed and/or limiting how long oxygen can be supplied to the mask.

The systems and methods described herein, using individual baseline blood-oxygen saturation levels for determining supplemental oxygen flow requirements, may maintain the equivalent level of safety and protection for all passengers or users regardless of their health or age. In various cases, the supplemental oxygen flow requirements based on the blood-oxygen saturation levels may be reduced compared to traditional oxygen flows because the detected blood-oxygen saturation levels factor in how a particular oxygen mask delivers oxygen and/or how the pulmonary system of the user works. In various cases, the embodiments described herein may provide an approximately 50% reduction in the amount of oxygen required to maintain the same level of protection for the passenger. This reduction in oxygen may allow for cost, weight, and storage savings, among others, because the provider of the oxygen may only need to supply about half the amount of oxygen for a given number of passengers. Conversely, a given quantity of oxygen may supply oxygen for a longer duration and/or may provide oxygen to about double the number of passengers for a given quantity of oxygen.

Example

Results from testing the control of the supply of oxygen are shown in the three charts below. In these test runs, ten different subjects (Subjects 1-10) having different health and physiology were tested to determine a baseline blood-oxygen saturation level at a baseline altitude of 14,000 ft. The blood-oxygen saturation level of each subject was then tested in a testing chamber at three simulated elevated altitudes: at a first elevated altitude of 20,000 ft. (Chart 1), a second elevated altitude of 25,000 ft. (Chart 2), and a third elevated altitude of 35,000 ft. (Chart 3). The time period for testing at each altitude was 120 seconds. At the first elevated altitude and as illustrated in Chart 1, the controller determined that, for each subject, a flow rate of 0.35 L/min. or 0.4 L/min. of the gas containing oxygen to each subject provided a detected blood-oxygen saturation level that was at least the baseline blood-oxygen saturation level for a particular subject. Similarly, at the second elevated altitude and as illustrated in Chart 2, the controller determined that, for each subject, a flow rate of 0.7 L/min. of the gas containing oxygen to each subject provided a detected blood-oxygen saturation level that was at least the baseline blood-oxygen saturation level for a particular subject. Likewise, at the third elevated altitude and as illustrated in Chart 3, the controller determined that, for each subject, a flow rate of 1.7 L/min. of the gas containing oxygen to each subject provided a detected blood-oxygen saturation level that was at least the baseline blood-oxygen saturation level for a particular subject. These results indicated that by controlling the flow of the gas containing oxygen based on the detected blood-oxygen saturation level and compared to a baseline blood-oxygen saturation level, a minimum flow of oxygen could be provided to each subject while also providing an equivalent level of safety despite the subjects having different health and physiology (i.e., the detected blood-oxygen saturation levels were all at least the baseline blood-oxygen saturation level for a particular subject).

CHART 1

Testing at 20,000 ft.

| Subject # | Baseline Blood-Oxygen Saturation Level (%) (at 14,000 ft.) | Mask Oxygen Flow (L/min.) | Blood-Oxygen Saturation Level at 20,000 ft. with Supplemental Oxygen Flow |
|---|---|---|---|
| 1 | 89 | 0.35 | 90 |
| 2 | 85 | 0.4 | 95 |
| 3 | 85 | 0.4 | 89 |
| 4 | 96 | 0.4 | 98 |
| 5 | 83 | 0.4 | 94 |
| 6 | 92 | 0.4 | 95 |
| 7 | 87 | 0.4 | 92 |
| 8 | 94 | 0.4 | 96 |
| 9 | 88 | 0.4 | 96 |
| 10 | 96 | 0.4 | 96 |

CHART 2

Testing at 25,000 ft.

| Subject # | Baseline Blood-Oxygen Saturation Level (%) (at 14,000 ft.) | Mask Oxygen Flow (L/min.) | Blood-Oxygen Saturation Level at 25,000 ft. with Supplemental Oxygen Flow |
|---|---|---|---|
| 1 | 89 | 0.7 | 92 |
| 2 | 85 | 0.7 | 98 |
| 3 | 85 | 0.7 | 94 |
| 4 | 96 | 0.7 | 97 |

CHART 2-continued

Testing at 25,000 ft.

| Subject # | Baseline Blood-Oxygen Saturation Level (%) (at 14,000 ft.) | Mask Oxygen Flow (L/min.) | Blood-Oxygen Saturation Level at 25,000 ft. with Supplemental Oxygen Flow |
|---|---|---|---|
| 5 | 83 | 0.7 | 96 |
| 6 | 92 | 0.7 | 99 |
| 7 | 87 | 0.7 | 96 |
| 8 | 94 | 0.7 | 98 |
| 9 | 88 | 0.7 | 100 |
| 10 | 96 | 0.7 | 97 |

CHART 3

Testing at 35,000 ft.

| Subject # | Baseline Blood-Oxygen Saturation Level (%) (at 14,000 ft.) | Mask Oxygen Flow (L/min.) | Blood-Oxygen Saturation Level at 35,000 ft. with Supplemental Oxygen Flow |
|---|---|---|---|
| 1 | 89 | 1.7 | 97 |
| 2 | 85 | 1.7 | 97 |
| 3 | 85 | 1.7 | 95 |
| 4 | 96 | 1.7 | 99 |
| 5 | 83 | 1.7 | 90 |
| 6 | 92 | 1.7 | 97 |
| 7 | 87 | 1.7 | 98 |
| 8 | 94 | 1.7 | 97 |
| 9 | 88 | 1.7 | 97 |
| 10 | 96 | 1.7 | 100 |

Illustrations

A collection of exemplary embodiments are provided below, including at least some explicitly enumerated as "Illustrations" providing additional description of a variety of example embodiments in accordance with the concepts described herein. These Illustrations are not meant to be mutually exclusive, exhaustive, or restrictive; and the disclosure not limited to these examples but rather encompasses all possible modifications and variations within the scope of the issued claims and their equivalents.

Illustration 1. A method of supplying oxygen to an oxygen mask for an aircraft, the method comprising: detecting, with at least one sensor and during a first time period, a first blood-oxygen saturation level at a first altitude; detecting, with the at least one sensor and during a second time period, a second blood-oxygen saturation level at a second altitude, wherein the second altitude is greater than the first altitude; and determining a minimum flow rate of a gas comprising oxygen for the second altitude such that the second blood-oxygen saturation level at least matches the first blood-oxygen saturation level at the same altitude.

Illustration 2. The method of any of the preceding or subsequent illustrations or combination of illustrations, further comprising: controlling, by a controller, a flow of the gas comprising oxygen to the oxygen mask such that the gas is supplied at the minimum flow rate.

Illustration 3. The method of any of the preceding or subsequent illustrations or combination of illustrations, wherein controlling the flow of the gas comprising oxygen comprises: determining a flow duration of the gas comprising a first concentration of oxygen such that the second-blood oxygen saturation level at least matches the first blood-oxygen saturation level; and controlling the flow of the gas such that the gas comprising the first concentration of oxygen is supplied to the oxygen mask for the flow duration, wherein the first concentration of oxygen is 100% oxygen.

Illustration 4. The method of any of the preceding or subsequent illustrations or combination of illustrations, wherein the flow duration is a first flow duration, and wherein controlling the flow of the gas comprising oxygen comprises: determining a second flow duration of the gas comprising a second concentration of oxygen, wherein the second concentration of oxygen is less than the first concentration of oxygen; and controlling the flow of the gas such that the gas comprising the second concentration of oxygen is supplied to the oxygen after the first flow duration and for the second flow duration.

Illustration 5. The method of any of the preceding or subsequent illustrations or combination of illustrations, wherein the first flow duration is less than the second flow duration.

Illustration 6. The method of any of the preceding or subsequent illustrations or combination of illustrations, wherein controlling the flow of the gas comprises supplying the gas at a flow rate from 0.2 L/min to 1.7 L/min.

Illustration 7. The method of any of the preceding or subsequent illustrations or combination of illustrations, wherein the second altitude is at least 12,000 feet.

Illustration 8. The method of any of the preceding or subsequent illustrations or combination of illustrations, further comprising generating an alert based on the second blood-oxygen saturation level being less than the first blood-oxygen saturation level.

Illustration 9. The method of any of the preceding or subsequent illustrations or combination of illustrations, further comprising: detecting, with the at least one sensor and during a third time period, a third blood-oxygen saturation level at a third altitude, wherein the third altitude is greater than the first altitude and greater than the second altitude; and determining a minimum flow rate of the gas comprising oxygen for the third altitude.

Illustration 10. The method of any of the preceding or subsequent illustrations or combination of illustrations, wherein the first time period and the second time period are each from 30 seconds to 180 seconds.

Illustration 11. The method of any of the preceding or subsequent illustrations or combination of illustrations, wherein at least one of the first time period or the second time period is 120 seconds.

Illustration 12. A method of supplying oxygen to an oxygen mask, the method comprising: simulating, with a testing system, an atmosphere at a first altitude; detecting, with a sensor, a blood-oxygen saturation level at the first altitude; and determining a minimum flow rate for the first altitude of a gas comprising oxygen such that the detected blood-oxygen saturation level at least matches a predetermined blood-oxygen saturation level.

Illustration 13. The method of any of the preceding or subsequent illustrations or combination of illustrations, further comprising controlling a flow of the gas to the oxygen mask such that the gas flows at the minimum flow rate and such that the detected blood-oxygen saturation level at least matches the predetermined blood-oxygen saturation level.

Illustration 14. The method of any of the preceding or subsequent illustrations or combination of illustrations, wherein controlling the flow of the gas comprises: determining a first flow of the gas comprising a first oxygen concentration and a first flow duration; determining a second flow of the gas comprising a second oxygen concentration and a second flow duration, wherein the second oxygen concentration is less than the first oxygen concentration; supplying the first flow of the gas comprising the first oxygen concentration for the first flow duration; and supplying the second flow of the gas comprising the second oxygen concentration for the second flow duration after the first flow duration.

Illustration 15. The method of any of the preceding or subsequent illustrations or combination of illustrations, wherein the first oxygen concentration is 100% oxygen, and wherein the first flow duration is less than the second flow duration.

Illustration 16. The method of any of the preceding or subsequent illustrations or combination of illustrations, wherein the detected blood-oxygen saturation level is a first detected blood-oxygen saturation level, and wherein the method further comprises: simulating, with the testing system, an atmosphere at a second altitude, wherein the second altitude is greater than the first altitude; detecting, with the sensor, a second blood-oxygen saturation level at the second altitude; and determining a minimum flow rate of the gas comprising oxygen for the second altitude such that the detected blood-oxygen saturation level at the second altitude at least matches the predetermined blood-oxygen saturation level.

Illustration 17. The method of any of the preceding or subsequent illustrations or combination of illustrations, wherein the predetermined blood-oxygen saturation level is at a predetermined altitude, and wherein the predetermined altitude is less than the first altitude.

Illustration 18. The method of any of the preceding or subsequent illustrations or combination of illustrations, wherein determining the minimum flow rate of the gas comprises determining a flow rate of 0.2 L/min to 1.7 L/min when the first altitude is less than or equal to 35,000 feet.

Illustration 19. The method of any of the preceding or subsequent illustrations or combination of illustrations, further comprising generating an alert based on the detected blood-oxygen saturation level being less than the predetermined blood-oxygen saturation level.

Illustration 20. The method of any of the preceding or subsequent illustrations or combination of illustrations, wherein determining the minimum flow rate of the gas to the oxygen mask comprises determining the minimum flow rate of the gas such that the detected blood-oxygen saturation level is at least 90% the predetermined blood-oxygen saturation level.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A method of supplying oxygen to an oxygen mask, the method comprising:
   testing the oxygen mask to verify that operation of the oxygen mask is compliant with TSO-C64b, the testing performed by:
   simulating, with a testing system that comprises a testing chamber separate from an aircraft, an atmosphere at a baseline altitude, wherein the baseline altitude is less than or equal to 14,000 ft.;
   detecting, with a sensor, a function of a pulmonary system including a baseline blood-oxygen saturation level for each user of a plurality of users at the baseline altitude; and
   determining a minimum continuous flow rate for a second altitude of a gas comprising oxygen for each user based on the function of the pulmonary system such that a detected blood-oxygen saturation level at the second altitude at least matches the baseline blood-oxygen saturation level, wherein the second altitude is greater than the baseline altitude; and
   controlling a flow of the gas to the oxygen mask for each user such that the gas flows at the minimum continuous flow rate for the second altitude and such that the detected blood-oxygen saturation level at least matches the baseline blood-oxygen saturation level for each user.

2. The method of claim 1, wherein controlling the flow of the gas comprises:
   determining a first flow of the gas comprising a first oxygen concentration and a first flow duration;
   determining a second flow of the gas comprising a second oxygen concentration and a second flow duration, wherein the second oxygen concentration is less than the first oxygen concentration;
   supplying the first flow of the gas comprising the first oxygen concentration for the first flow duration; and
   supplying the second flow of the gas comprising the second oxygen concentration for the second flow duration after the first flow duration.

3. The method of claim 2, wherein the first oxygen concentration is 100% oxygen, and wherein the first flow duration is less than the second flow duration.

4. The method of claim 1, further comprising:
   simulating, with the testing system, an atmosphere at a third altitude, wherein the third altitude is greater than the baseline altitude;
   detecting, with the sensor, a blood-oxygen saturation level at the third altitude; and
   determining a minimum flow rate of the gas comprising oxygen for the third altitude such that the detected blood-oxygen saturation level at the third altitude at least matches the baseline blood-oxygen saturation level.

5. The method of claim 1, wherein determining the minimum continuous flow rate of the gas comprises determining a flow rate of 0.2 L/min to 1.7 L/min when the second altitude is less than or equal to 35,000 feet.

6. The method of claim 1, further comprising generating an alert based on the detected blood-oxygen saturation level being less than the baseline blood-oxygen saturation level.

7. The method of claim 1, wherein determining the minimum continuous flow rate of the gas to the oxygen mask comprises determining the minimum continuous flow rate of the gas such that the detected blood-oxygen saturation level is at least 90% the baseline blood-oxygen saturation level.

* * * * *